(12) United States Patent
Francesco (10) Patent No.: US 8,865,092 B2
(45) Date of Patent: Oct. 21, 2014

(54) FIXATION AND STORAGE OF BIOLOGICAL ORGANIC SAMPLES

(75) Inventor: Visinoni Francesco, Mozzo (IT)

(73) Assignee: Milestone S.r.l., Sorisole (BG) (IT)

( * ) Notice: Subject to any disclaimer, the term of this patent is extended or adjusted under 35 U.S.C. 154(b) by 294 days.

(21) Appl. No.: 13/451,287

(22) Filed: Apr. 19, 2012

(65) Prior Publication Data

US 2012/0294782 A1 Nov. 22, 2012

(30) Foreign Application Priority Data

May 19, 2011 (EP) ..................................... 11166751

(51) Int. Cl.
*B01L 9/00* (2006.01)
*A01N 1/00* (2006.01)
*G01N 1/31* (2006.01)
*A61G 12/00* (2006.01)
*B01L 3/00* (2006.01)
*G01N 35/00* (2006.01)

(52) U.S. Cl.
CPC ................ *A01N 1/00* (2013.01); *A61G 12/001* (2013.01); *G01N 1/31* (2013.01); *B01L 3/505* (2013.01); *G01N 2035/00217* (2013.01)
USPC ................ 422/561; 422/63; 422/64; 422/65; 422/67; 436/180

(58) Field of Classification Search
CPC ...... G01N 1/00; G01N 1/36; G01N 2001/305
USPC ............................... 422/63–67, 561; 436/180
See application file for complete search history.

(56) References Cited

U.S. PATENT DOCUMENTS

| 7,879,000 B2 * | 2/2011 | Behague et al. ............. 604/6.07 |
| 2009/0191533 A1 | 7/2009 | Bussolati |

FOREIGN PATENT DOCUMENTS

| DE | 10117205 A1 | 10/2002 |
| EP | 2070410 A1 | 6/2009 |

OTHER PUBLICATIONS

Hewitt et al., "Tissue Handling and Specimen Preparation in Surgical Pathology," retrieved at <<http://www.archivesofpathology.org/doi/pdf/10.1043/1543-2165-132.12.1929>>, Arch Pathol Lab Med—vol. 132, Dec. 2008, 7 pages.

"IARC, Monographs on the Evaluation of Carcinogenic Risk to Humans." International Agency for Research on Cancer, 2006, IARC, vol. 88, Lyon, France, retrieved at <<http://monographs.iarc.fr/ENG/Monographs/vol88/mono88.pdf>>, Part 1, 119 pages.

(Continued)

*Primary Examiner* — Jyoti Nagpaul
(74) *Attorney, Agent, or Firm* — Lee & Hayes, PLLC (57) ABSTRACT

A method for automatically dosing a fixative solution in a flexible bag containing at least one biological organic sample comprises placing the bag with the sample in a dosing system (e.g., on a holder or weighing device), computing a required volume or weight of fixative solution as a function of the sample or the bag with the sample, and automatically transferring the computed volume or weight of fixative solution from a storage container into the bag. A system is also described for automatically dosing a fixative solution in a flexible bag containing at least one biological organic sample, a carrier for said flexible bags, and a storage cabinet for storing the carrier.

6 Claims, 10 Drawing Sheets

(56) References Cited

OTHER PUBLICATIONS

"IARC, Monographs on the Evaluation of Carcinogenic Risk to Humans." International Agency for Research on Cancer, 2006, IARC, vol. 88, Lyon, France, retrieved at <<http://monographs.iarc.fr/ENG/Monographs/vol88/mono88.pdf>>, Part 2, 116 pages.

"IARC, Monographs on the Evaluation of Carcinogenic Risk to Humans." International Agency for Research on Cancer, 2006, IARC, vol. 88, Lyon, France, retrieved at <<http://monographs.iarc.fr/ENG/Monographs/vol88/mono88.pdf>>, Part 3, 111 pages.

"IARC, Monographs on the Evaluation of Carcinogenic Risk to Humans." International Agency for Research on Cancer, 2006, IARC, vol. 88, Lyon, France, retrieved at <<http://monographs.iarc.fr/ENG/Monographs/vol88/mono88.pdf>>, Part 4, 86 pages.

"IARC, Monographs on the Evaluation of Carcinogenic Risk to Humans." International Agency for Research on Cancer, 2006, IARC, vol. 88, Lyon, France, retrieved at <<http://monographs.iarc.fr/ENG/Monographs/vol88/mono88.pdf>>, Part 5, 50 pages.

* cited by examiner

FIXATION AND STORAGE OF BIOLOGICAL ORGANIC SAMPLES

This Application claims foreign priority to European Patent Application No. 11166751.5, filed May 19, 2011, which is incorporated herein by reference.

TECHNICAL FIELD

This invention generally relates to the preanalytical field of investigation of biospecimen (in the following also referred to as specimen or biological organic sample or sample). It is in the period after removal by surgery of biospecimen, fixation of the same as well as long time storage.

This invention relates to a method and a system for automatically dosing a fixative solution in a flexible bag containing at least one biological organic sample. The invention is thus particularly directed to a method and to a semi-automatic and/or automatic device or system for sealing a biospecimen preferably under vacuum, with a (user-)preset amount of fixative, normally 10% NBF formalin but not limited to this reagent, this ration based on the actual weight of the specimen to be preserved. The invention further relates to a carrier for said flexible bags as well as a storage cabinet for storing said carrier.

DESCRIPTION OF THE BACKGROUND ART

Standard practices in operating room calls for delivering to the operating theater, containers of different shapes/volume prefilled with a fixative, in the large majority of cases NBF formalin 10%. During the operation biospecimens from the patient must be placed by the nurses in such containers. Opening the container in the operating room exposes the operating room team to the toxic and cancer-provoking fumes of formalin.

The declaration recently issued by the International Agency for Research on Cancer (International Agency for Research on Cancer (2006), Monographs on the evaluation of Carcinogenic Risk to humans. (IARC, Vol. 88) Lyon, France), which classified formaldehyde as a Class 1 carcinogenic has increased the request by health authorities, technicians and practicing pathologists to entirely avoid or at least substantially reduce contact with formalin. The standard use of formalin (formaldehyde) as well as other fixative reagents is encountering increasing criticisms because of toxicity and environmental concerns.

Several other disadvantages are present in this sequence of events:
1) Often biospecimens are not placed immediately in the fixative solution. Remaining exposed to air damages the integrity of the tissue and the subsequent morphology when examining the slide at the microscope.
2) The ratio sample/fixative, according to literature ("Tissue handling and specimen preparation in surgical pathology" Stephen M. Hewitt etc) of 1:10 in weight or volume cannot be defined as containers are prefilled and specimens are not weighed, i.e. the volume of fixative in the prefilled container is preset independent of the weight of the biospecimen. In practice, the average ratio sample/fixative is about 1:20 to 1:25.
3) Standard containers are heavy and bulky. The containers have plastic lids which do not perfectly seal the containers. Thus, evaporation of formalin fumes can take place.
4) In case of spilling of a container, the operating room must be closed and sterilization procedure must be carried out.
5) Outside the operation room the containers, with their large volume and weight, must be transferred using separate trolleys from the operating theatre to the histology lab.

After arrival in the histology lab, the pathologist or the pathologist assistant opens the container under a fume hood and gross the specimen for further processing.

The remaining bulk of the biospecimen is placed back in the container with formalin and, at the end of the shift, transferred in a special storage room for a preset period of time, normally 2 to 3 weeks, for eventual further need. The storage rooms must thus be ventilated.

Some of the disadvantages of this method are as follows:
1) The biospecimens during storage can release fermentation gases which can cause the lid to open and subsequently the formalin evaporates in the atmosphere of the room.
2) Because of the closed containers specimens are difficult to recognize and very bulky to manipulate.
3) Due to mechanical action the lid can open sometime and causes evaporation of formalin in the atmosphere. This may result in the biospecimens to dry out and thus to damage their morphology.
4) When biospecimens contains air (e.g. lung) the specimen can float on the surface and therefore not all surfaces are wetted by the fixative.

EP 2 070 410 A1 shows a method for preserving a fresh biospecimens under vacuum in a sealed bag which is filled with a protective gas when the minimum vacuum level is reached. The specimens are kept at 4° C. and transferred to the histology lab. Here the bags are opened and the specimen is grossed as "fresh".

The specimen must then be fixed in either formalin, a molecular fixative or frozen for tissue banking, according to the requirements of the users.

OBJECT AND SUMMARY OF THE INVENTION

It is thus an object of the invention to provide a method and system as well as a carrier device and storage cabinet to improve the quality of the process of fixation and storage of biospecimens.

The object is achieved by means of the features of the independent claims. The dependent claims develop further the central idea of the present invention.

According to a first aspect, the invention relates to a method for automatically dosing a fixative solution in a flexible bag containing at least one biological organic sample, the method comprising the steps of:
a) placing the bag with the sample in a dosing system, preferably on a holder, more preferably on a weighing device of said system,
b) computing the required volume or weight of fixative solution as a function of the sample or the bag with the sample, and
c) automatically transferring the computed volume or weight of fixative solution from a storage container into the bag.

According to the invention, the volume/weight, i.e. the dosage of the fixative is determined for each specimen singularly and individually. This assures a minimum amount of fixative used for fixation while at the same time enough fixative mass is available for proper fixation. The method thus describes a user's defined or pre-defined or pre-calculated fixation method which allows the same fixative/specimen weight or volume ratio to be standardized and above all documented for improved quality control. It is noted that the dosage of the fixative can be linearly or non-linearly with respect to the weight of a particular biospecimen. The method thus also gives consideration to such dependencies. The dosage of the fixative is thus specific to the sample.

The method of the present invention reduces by over 30% the weight and the space required for the long term storage of the biospecimens. The limited amount of fixative (e.g. formalin) in the bag will eliminate the separation formalin/biospecimens required for standard disposal.

Step c) can be followed by step d) of evacuating or preferably automatically evacuating the flexible bag. In a very preferred embodiment, the flexible bag is evacuated by evacuating a sealably closed treatment chamber of the system housing the flexible bag, preferably housing the flexible bag on the weighing device, or evacuating the flexible bag itself preferably being placed on the weighing device. Further, step c) or step d) can be followed by step e) of sealing or preferably automatically sealing the flexible bag. For the sealing step, the flexible bag can remain in the sealably closed treatment chamber, particularly in case of a preceding evacuation step also carried out in the treatment chamber.

The method thus allows an evacuation of flexible bags with the presence of liquids inside the bag itself. With vacuum sealing, the fixative is in "intimate" contact with the specimen thus coating the external surface in a perfect way. Further, no protective gas is needed since the only gas inside the flexible bag can be or is a saturated fixative vapour. The sealed flexible bag also guarantees a constant volume of fixative even after months or years in comparison with a standard bucket where the fixative can be reduced due to evaporation of the same. The sealed flexible bag eliminates the possibility of spilling if the container should fall on the floor. Furthermore, a storage room does not need to be ventilated with a remarkable reduction of costs.

Hence, with an evacuated and sealed bag a standardized and documented sealing fixation, transfer and storage of biospecimens in a fixative under vacuum conditions can be achieved. The vacuum sealing of biospecimens can also be carried out with a preset ratio of a fixative solution. The dosage of the fixative is thus determined individually and specific to the sample.

A fixative solution delivery means, preferably a delivery nozzle, for discharging the computed volume or weight of fixative solution automatically transferred from the storage container into the bag can be moved between a delivery position, in which the delivery means extends into the flexible bag, and a sealing or retracted position, in which the delivery means is retracted from the flexible bag. It is thus easy to transfer fixative into the bag. When being finished, the opening of the bag can be released from the delivery means thus making it easy to remove the flexible bag from the system or enabling a (automatic) sealing of the bag without further manipulating the bag.

A control unit preferably controls the computing in step b), preferably controls a pump for the automatic transfer in step c), preferably controls an evacuation means for the automatic evacuation in step d), preferably controls a sealing means for the automatic sealing in step d), and preferably controls the movement of the delivery means between the delivery position and the sealing or retracted position. Hence, the method can be carried out semi-automatic or even fully automatic.

Preferably, the method or at least step c) of the method described above is carried out in a sealed treatment chamber which also comprises the weighing device. As the fixative is delivered into the flexible bag in a closed and sealed environment no vapours are released and therefore a higher safety standard is assured for the operator. This effect is even improved in case the whole process, i.e. after placing the bag on the weighing device and before removing the bag including the biospecimen and fixative and preferably being evacuated and/or sealed, is carried out in the sealably closed treatment chamber.

According to another aspect, the invention refers to a system for automatically dosing a fixative solution in a flexible bag containing at least one biological organic sample, wherein the system comprises a holder for holding a flexible bag containing the sample upright in the system, and a control unit controlling a pump in order to transfer an amount of fixative solution from a storage container into the bag. In a preferred embodiment, the system further comprises a weighing device, wherein the holder is designed for holding the flexible bag containing the sample upright on said weighing device.

It is thus possible to provide a semi-automatic and/or fully automatic device or system for sealing a biospecimen with a (user-)preset or pre-calculated amount of fixative, normally 10% NBF formalin but not limited to this reagent, this ration based on the actual weight of the specimen to be preserved. It is also referred to the advantages achieved by the inventive method according to the first aspect of the invention which apply mutatis mutandis to the system according to the second aspect of the invention.

The weighing device can comprise a load cell. Hence, an accurate weighing device is provided which can also be easily controlled by a control unit for automatic weighing.

The holder (preferably a cage for receiving the flexible bag) is preferably attached to the weighing device in a fixed or removable manner. Hence, the bag can be accurately weight when just being placed in the holder. In case of a removable holder, the holder can be easily cleaned or replaced to be adapted to the dimensions or contour of the flexible bag or biospecimen inside the bag.

The weighing device can be a device for volumetrically and/or gravimetrically weighing.

The system preferably comprises means for evacuating the bag. The system may also comprise means for sealing the bag. The evacuation means and/or the sealing means are preferably controllable or controlled by the control unit. In respect of the advantages achieved by the evacuation and sealing of the bag, it is referred to the respective method steps described above, which advantages apply mutatis mutandis to the corresponding system.

The system may still further comprise a fixative solution delivery means, preferably a delivery nozzle, for discharging the amount of fixative solution transferred from the storage container into the flexible bag, wherein the delivery means is designed to be moveable between a delivery position, in which the delivery means extends into the flexible bag, and a sealing or retracted position, in which the delivery means is retracted from the flexible bag.

According to still another aspect of the invention, a carrier for flexible bags containing at least one biological organic sample in a fixative solution is provided, wherein the carrier comprises a frame for holding the flexible bag and a reservoir at the bottom of the frame and preferably integrally formed with the frame, wherein the reservoir is dimensioned and, with respect to the frame, arranged such that any leakage of the flexible bag can be collected inside the reservoir.

By means of such a carrier, the flexible bags can be easily stored and handled while providing a collecting means for any leaking fixative for the unlikely case that one of the flexible bags is damaged. Since each of the carriers comprises such a reservoir, spilling of fixative can be avoided independent from the location of the carrier (i.e. in a storage device or when being handled).

The carrier may further comprise a holding means, preferably a clip, for attaching the flexible bag to the frame of the carrier such that the flexible bag is arranged above and/or at least partially inside the reservoir. It is thus easy to attach the flexible bag to the carrier the correct way.

Preferably, the frame further comprises hanging means for hanging the carrier on and/or in a storage device. Hence, the carrier can be fitted to a storage cabinet or transfer trolley and easily stored, e.g., in hanging files type.

The carrier may further comprise identification means. The identification means are preferably removably attached to an exposed part of the frame of the carrier. The identification means can be a tag, like a hand-written tag or a Bar Code label or a Quick Response (QR) Code label, or a chip, like an RFID-chip, or the like. It is thus easy to document the biospecimen as well as the fixative/specimen ratio and thus standardize said ratio for an improved quality control.

According to still another aspect, the invention relates to a storage cabinet for storing the carrier according to the invention, the storage cabinet comprises receiving means for receiving the hanging means of the carrier for storing the carrier in a hanging files type, the storage cabinet preferably comprising wheels forming a transfer trolley to be moveable. Hence, a plurality of carriers can be stored in a single storage cabinet or transfer trolley, e.g., in hanging files type. When having wheels, a plurality of carriers can further be easily transferred at once.

The storage cabinet may further comprise a ventilation or exhaust system for ventilating the preferably closed storage cabinet. Since the cabinet itself is ventilated, no ventilated rooms are required.

BRIEF DESCRIPTION OF THE DRAWINGS

Further features, advantages and objects of the present invention will become apparent for a skilled person when reading the following detailed description of the embodiments of the present invention, when taken in conjunction with the figures of the enclosed drawings.

DETAILED DESCRIPTION OF THE EMBODIMENTS

Figure 1A:
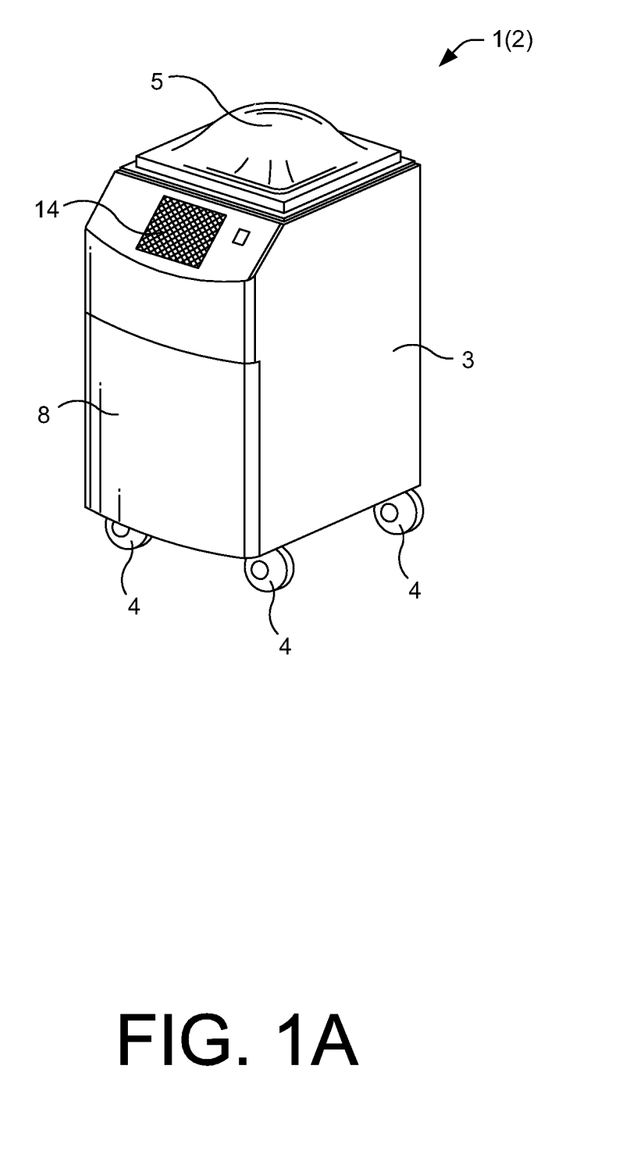
FIG. 1a shows a system for automatically dosing a fixative solution in a flexible bag containing a biological organic sample according to a first embodiment of the invention and having a cover being closed.
Figure 1B:
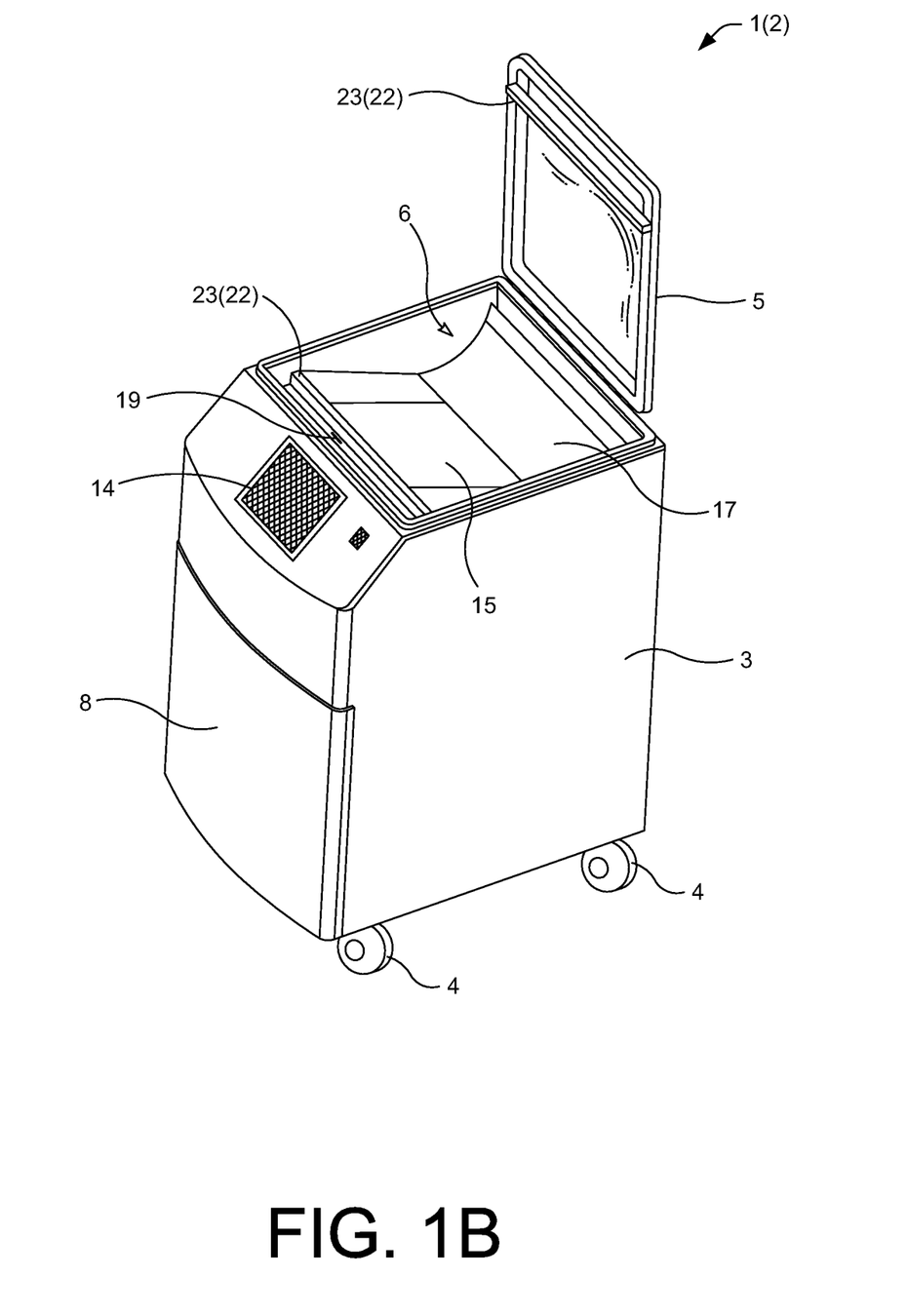
FIG. 1b shows the system of FIG. 1a having the cover being opened.

FIGS. 1a and 1b show a (dosing) system 1 or device for automatically dosing a fixative solution F in a flexible bag 15 containing a biological organic sample 18 according to a first embodiment of the invention. The system 1 can preferably be designed as a trolley 2 having a casing or housing 3. The trolley 2 can be provided with a plurality of wheels 4 to be easily movable.

Figure 2:
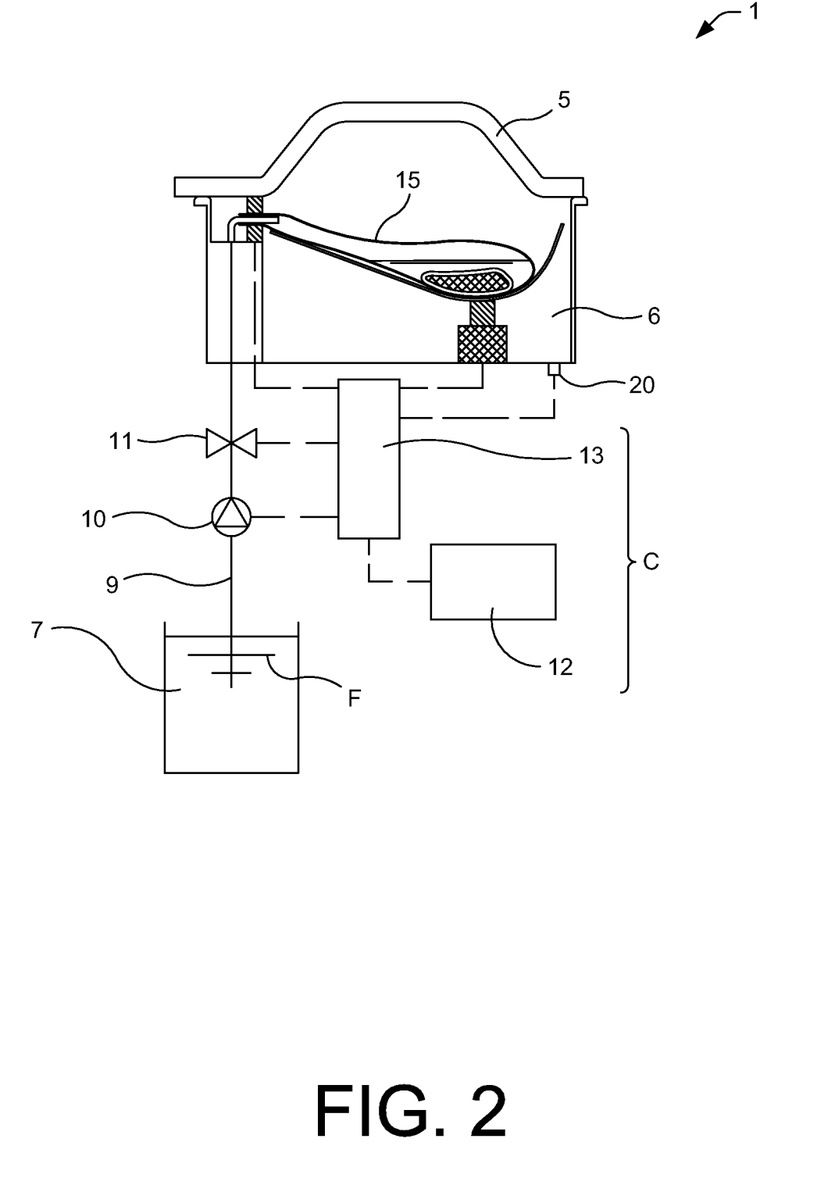
FIG. 2 shows a schematic drawing of the system of FIGS. 1a and 1b.

The system 1 can further comprise a cover 5 for covering, preferably sealably covering a treatment chamber 6 as, for instance, shown in FIG. 1b as well as FIG. 2 showing a schematic drawing of the system 1 of FIGS. 1a and 1b.

The system 1 comprises a storage container 7 holding a fixative F, e.g. formaldehyde. The storage container 7 is accessible and thus preferably replaceable via an opening in the housing 3 of the system 1 which can be (sealably) closed by a door 8.

A (fixative) delivery line 9 connects the storage container with the treatment chamber 6, particularly with the flexible bag 15 when being placed in the system 1 or better in the treatment chamber 6 (if present) as described below. To allow a delivery of the fixative F from the storage container 7 into the treatment chamber 6, the delivery system, preferably delivery line 9, is provided with a pump 10 as well as a valve 11 being provided downstream of the pump 10. The pump 10 and the valve 11 can be controlled by a control unit C preferably comprising a controller 12 (as a user interface) as well as a central processing unit (CPU) 13. Therefore, the pump 10 and the valve 11 are connected to the CPU 13 which in turn is connected to the controller 12. According to the invention, the control unit C controls the pump 10 in order to (automatically) transfer an amount of fixative solution F from the storage container into the treatment chamber 6, particularly into a flexible bag 15 as will be described in detail in the following. The valve 11 can be controlled by the control unit C for controlling the amount and flow rate of the delivered fixative F. It is noted that the invention is not limited to the described delivery system but can also be arranged and equipped in a different way as long as a preferably controlled transfer of fixative F is enabled.

The system 1 further comprises a user interface, e.g. a touch screen 14, such that the user can easily operate the controller 12, particularly the system 1 and respective process.

Figure 3:
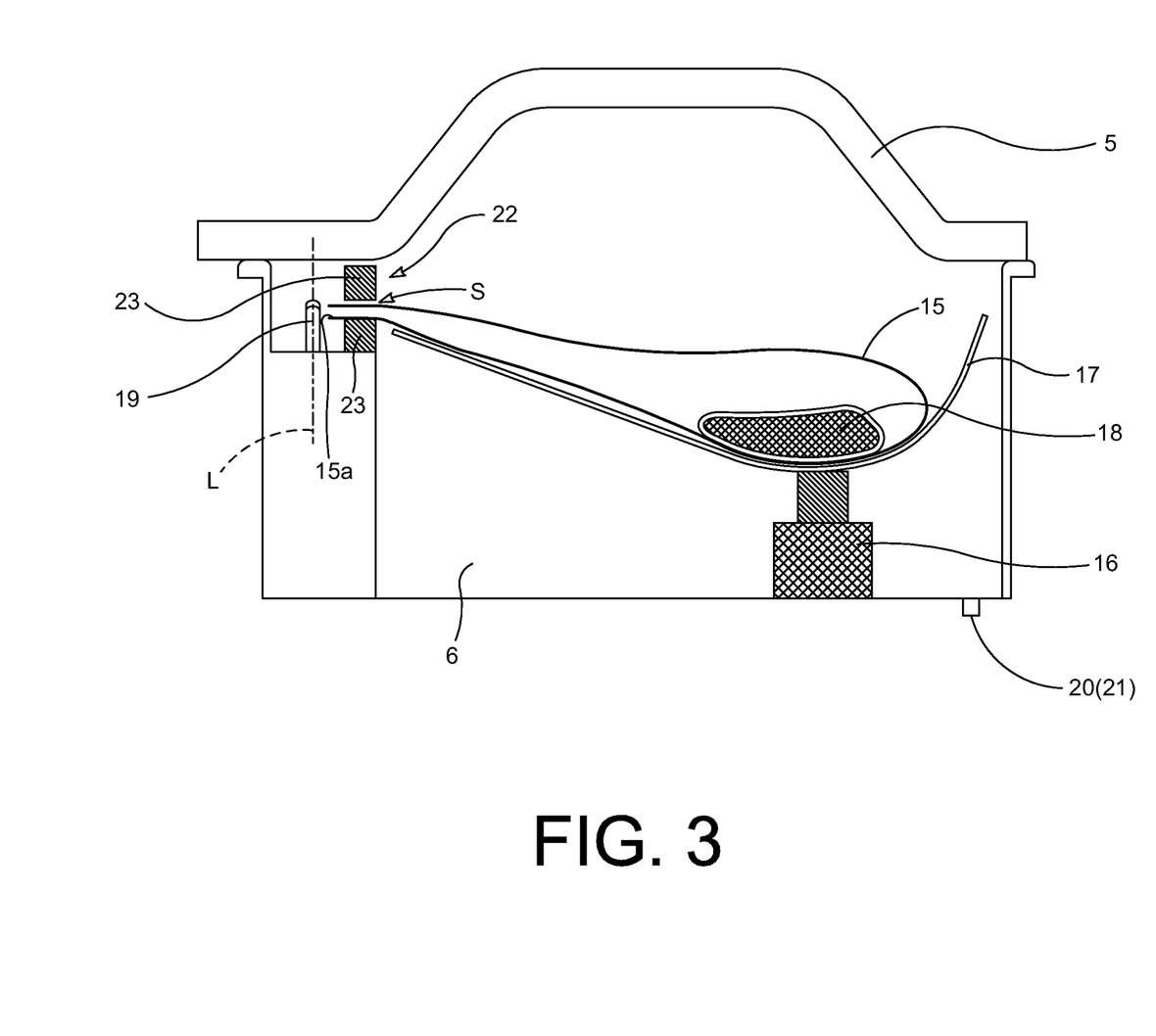
FIG. 3 shows a partial view of the system of FIG. 2 according to a first step of a method according to the invention.
Figure 4:
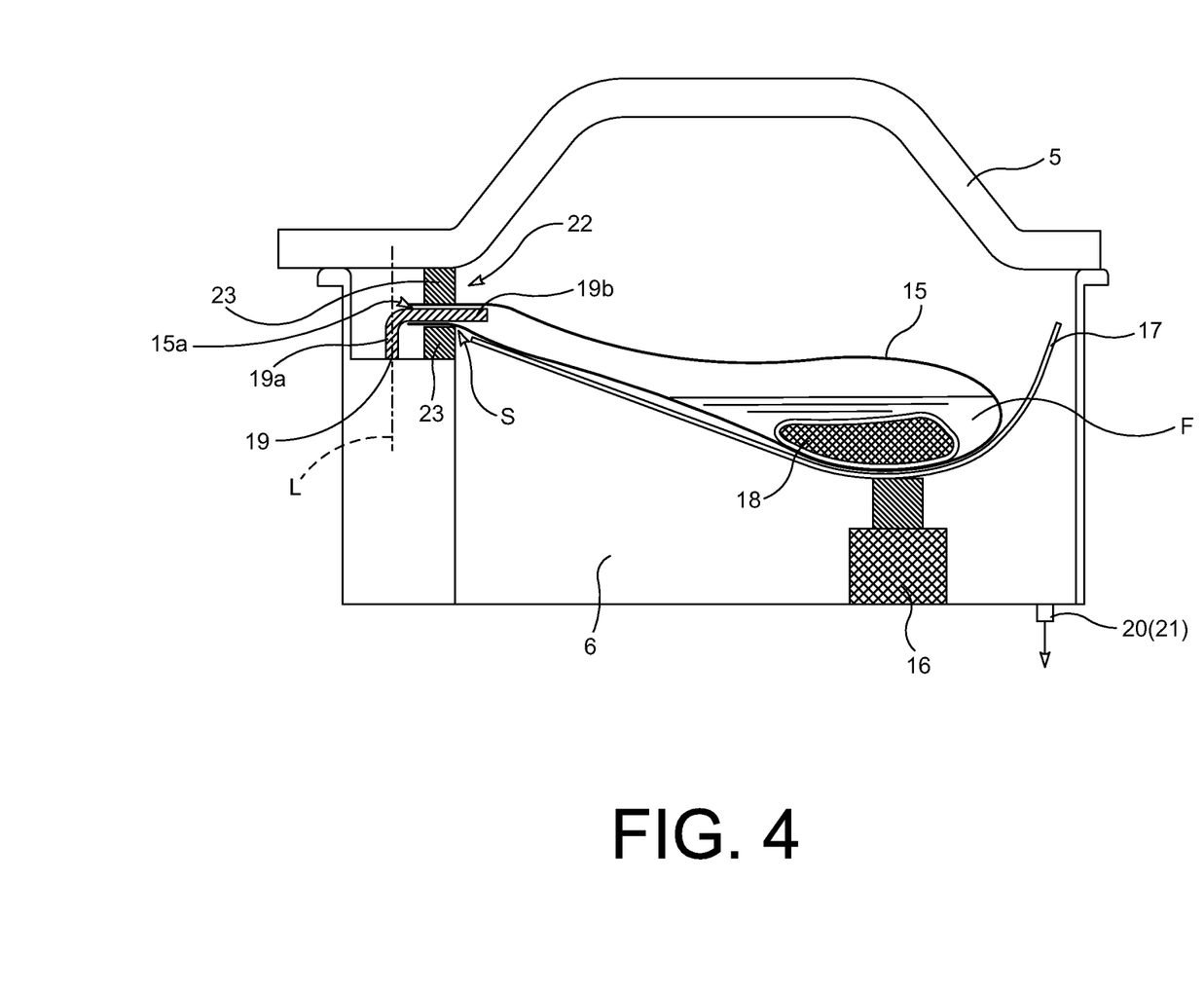
FIG. 4 shows the partial view of FIG. 3 of the system of FIG. 2 according to a second step of a method according to the invention.
Figure 5:
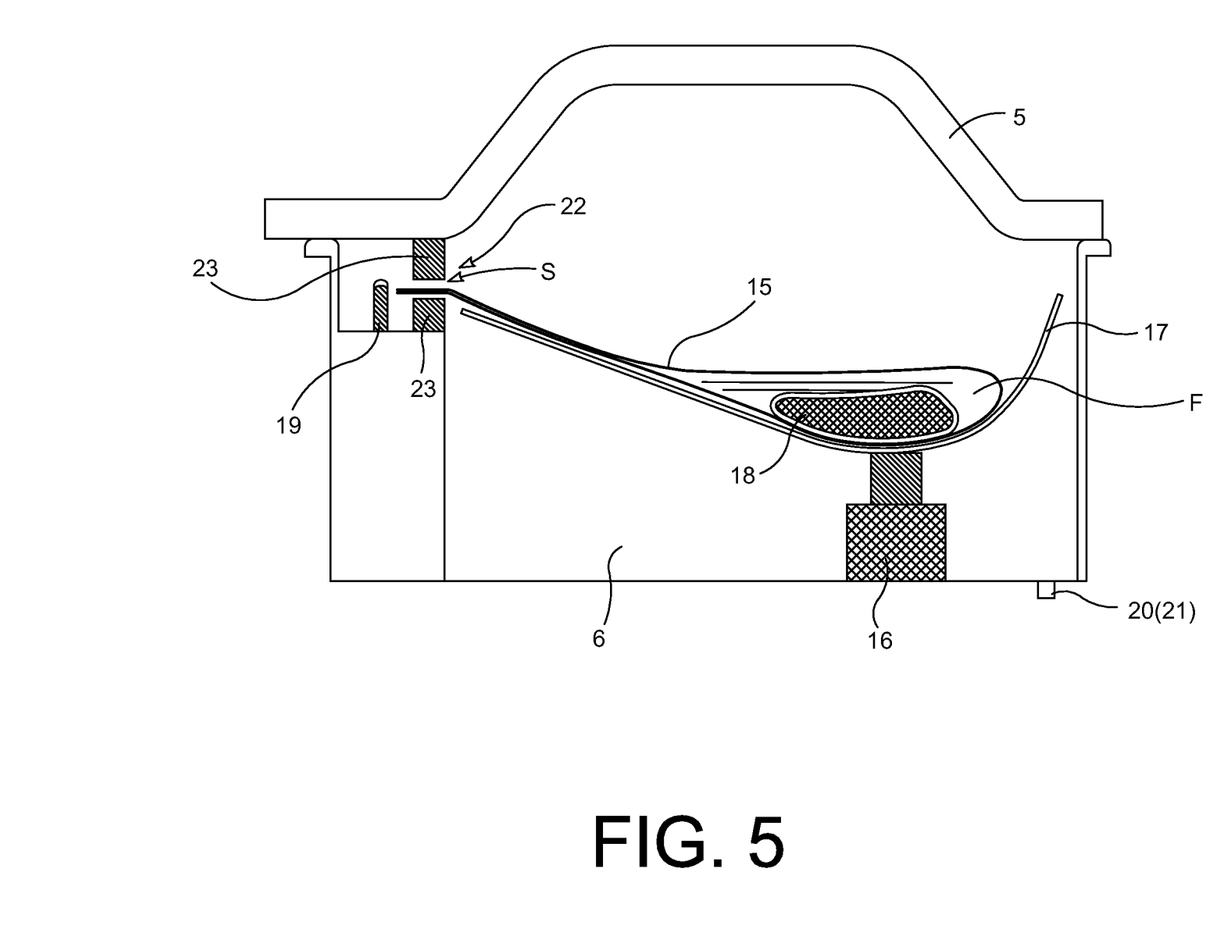
FIG. 5 shows the partial view of FIG. 3 of the system of FIG. 2 according to a third step of a method according to the invention.

FIGS. 3 to 5 show a partial view of the system of FIG. 2 according to the invention. In FIGS. 3 to 5, the treatment chamber 6 being selectively coverable by the cover 5 is shown. As has been described above, the treatment chamber 6 is preferably sealably closable by said cover 5. Therefore, sealing means can be provided between the cover 5 and the treatment chamber 6 in a closed condition. Due to the closed and sealed environment no vapours can released and therefore a higher safety standard is assured for the operator.

The system can further comprise a weighing device 16 for volumetrically and/or gravimetrically weighing. In a preferred embodiment, the weighing device 16 comprises a load cell for easily converting a force (i.e. the weight of a biospecimen) into an electrical signal which can then be used for computing a particular amount, i.e. weight or volume of a fixative solution F to be delivered into the flexible bag 15 as will be described below. The weighing device 16 is preferably connected to the control unit C, particularly to the CPU 13, to allow an accurate weighing and control of the system.

The system 1 further comprises a holder 17 for holding the flexible bag 15 containing at least one biological organic sample 18. The holder is designed such that the flexible bag 15 is held in the system 1 or better on the weighing device 16 in an upright position. According to the invention, the term "upright" is not to be equated with the term "vertical" but means that the flexible bag 15 is held in the holder 17, i.e. on the weighing device 16, such that the opening 15a of the bag 15 is positioned at the uppermost position in a vertical direction and with respect to the flexible bag body, as can be seen, for instance, in FIGS. 2 to 5. Hence, no fixative F can flow out of the bag 15 while the fixative F is transferred into the bag 15.

The holder 17 can be formed as a cage for receiving the flexible bag 15. Preferably, the contour or dimensions of the holder 17 can be adapted to the contour or dimensions of the flexible bag 15 (or the biospecimen 18) being used for the respective fixation operation. In case the system 1 comprises a weighing device 16, the holder 17 can be fixed to the weighing device 16 or can be attached to the weighing device 16 in a removable or detachable manner.

The flexible bag 15 is preferably made of a plastic material and can be transparent. Due to the transparency of the flexible bag 15, the specimens 18 can be easily recognized in comparison to the non-transparent standard buckets commonly used in the prior art. The bags 15 may further be fitted with pockets to include a requisition form or other documentation. Also a Bar Code label or a QR Code label can be added into said pocket which can be scanned by a scanner (not shown) of the system 1. Hence, the system 1 can be provided with useful data regarding the content (i.e. biospecimen) for further improving the process.

At the end of the delivery line 9 being opposite to the storage container 7, the delivery line 9 is provided with a delivery means 19 reaching into the treatment chamber 6, particularly into the flexible bag 15 when being placed in the system 1, i.e. preferably on the holder and/or the weighing device 16. The delivery means 19 can be or comprise a delivery nozzle as shown in FIG. 4. The delivery means 19 is designed such that it extends into the flexible bag 15 during a transferral of fixative solution F from the storage container 7 such that the fixative solution F can be (automatically) transferred into the flexible bag 15. Therefore, the flexible bag 15 is to be placed in or on the holder 17 such that the delivery means 19 can extend into the opening 15a of the flexible bag 15 while at the same time the flexible bag 15 is completely held by the holder 17 being preferably attached to the weighing device 16 (see FIG. 4) for an accurate weighing of a fixative/specimen ratio.

The system further comprises evacuation means 20 for evacuating the flexible bag 15. Therefore, a vacuum connection 21 can be provided to the system 1 such that the air or any gases, like pathological gases or formalin gases, can be withdrawn by suction. The vacuum connection 21 can be a nozzle which can be connected to an evacuation device (exhaust system) of the evacuation means via a hose or tube or the like. The evacuation means 20 can be controlled by the control unit C, preferably for an automatic evacuation of the treatment chamber 6 or better of the flexible bag 15.

In case the (sealably closed) treatment chamber 6 is evacuated, the flexible bag 15 will be evacuated as well. It is noted that in FIGS. 2 to 5 there is merely shown the vacuum connection 21. It is understood that the evacuation means 20 may further comprise any known exhaust device for withdrawing the gases off the treatment chamber 6. Further, a filtering means or the like can be provided (e.g. in the nozzle 21 or a hose or tube connecting the vacuum connection 21 with an exhaust system) as well for filtering any toxic gases/particles, like formalin gases or the like, off the sucked air. Also, the positioning and equipment of the evacuation means 20 or vacuum connection 21 is not limited by the shown embodiments but can be arranged anywhere at or in the system 1 as long as an evacuation of the flexible bag 15 can be carried out. The evacuation means 20 may also comprise a nozzle or hose (not shown) extending directly into the flexible bag 15.

The system 1 may further comprise a sealing means 22 for sealing the flexible bag 15. The sealing means 22 can be, for instance, sealing bars 23, 23. According to the embodiment of FIG. 1b, there is one sealing bar 23 being provided at the cover 5 while the other sealing bar 23 is arranged close to the delivery means 19 inside the treatment chamber 6. The latter sealing means 23 is preferably arranged between the holder 17 and the delivery means 19. In case the cover 5 is closed for carrying out the process, the sealing bars 23, 23 are arranged next to each other and form a slit or opening S there between through which the end of the flexible bag 15 having the opening 15a can be or is inserted as shown in FIGS. 2 to 5. The arrangement of the sealing bars 23, 23, however, is not limited by the embodiment of the invention. It is also possible that both the sealing bars 23, 23 are arranged inside the treatment chamber 6 as, for instance, shown in FIG. 3. The sealing bars 23, 23 can be moveable relative towards each other (i.e. at least one sealing bar 23 can be moved towards the other sealing bar 23) thus applying a clamping force onto the bag 15 (preferably close to its opening 15a as shown in FIGS. 2 to 5) for enhancing the sealing treatment as described in the following.

By heating the bag 15, preferably close to its opening 15a, the flexible bag 15 will be heat treated and thus sealed as the (plastic) material of the flexible bag 15 merges. In addition, during the heat treatment of the sealing means 22, the sealing bars 23, 23 can also be moved relatively towards each other thus increasing the merging of the bag 15 to be sealed. Even if the embodiments show sealing bars 23, 23 for a heat treated sealing of the flexible bag 15, the invention is not limited to such sealing means or operation. The sealing of the bag can also be attained by agglutinating the opening 15a of the bag 15 or by any other known sealing method. The sealing means 22 can preferably be controlled by the control unit C for an automatic sealing of the flexible bag 15.

The fixation step (transfer of fixative F into the bag 15), the evacuation step as well as the sealing step can preferably be carried out subsequently while the treatment chamber 6 is sealably closed during the whole process steps thus avoiding any fumes or vapours to release the system 1.

To allow an easy sealing of the flexible bag 15, the delivery means 19, i.e. the delivery nozzle, can be designed such that it is movable between a delivery position in which the delivery means 19 extends into the flexible bag 15 (as can be seen in FIG. 4), and a sealing or retracted position in which the delivery means 19 is retracted from the flexible bag 15 (as can be seen in FIG. 5). Therefore, the delivery nozzle 19 can be bent by an angle of about 90° (but is not limited to 90° but can have any desired angle) and can be turnable or rotatable about the longitudinal axis L of its upstream end 19a such that its bended downstream end 19b can be selectively moved into and out of the flexible bag 15. The delivery nozzle 19 can thus be rotatable about an angle big enough to allow the nozzle 19 to be retracted from the flexible bag 15 and extend into the flexible bag 15, i.e. about an angle of preferably 90° to 180°. The delivery means 19 can also be connected to the control unit C (not shown) to automatically control the movement of the delivery means 19 for a fully automatic process.

In a preferred embodiment and as can be seen in FIG. 4, the sealing means 22, i.e. the sealing bars 23, 23, should be arranged during a delivery position of the delivery means 19 such that the opening S between the sealing bars 23, 23 allow the delivery means 19 to be arranged there between with its upstream end 19a thus allowing a delivery of fixative F into the flexible bag 15.

It is noted that in case the evacuation means 20 also comprises a nozzle or hose extending directly into the flexible bag 15, said nozzle or hose can be designed and movable the same way as the delivery means 19 described above.

In the following, a method for fixating a biological organic sample 18 will be described.

A user, e.g. an operation room nurse, places the biospecimen 18 in the flexible bag 15 and transfers it from the operation room to the adjacent so-called "dirty room".

In step 1 (placing, (weighing) and calculating step) as shown in FIG. 3, the flexible bag 15 containing the at least one biological organic sample 18 is then placed with the sample 18 on a weighing device 16, more precisely on a holder 17 attached to the weighing device (e.g. a load cell) 16 that detects the weight of the specimen 18 or the weight of the specimen 18 and the flexible bag 15.

It is noted, that the holder 17 does not necessarily be attached to the weighing device 16, i.e. that no weighing device 16 is provided in the system 1. In this case, the weight of the specimen 18 or the weight of the specimen 18 and the flexible bag 15 can be determined/weighed before placing the flexible bag 15 containing the sample 18 onto the holder 17. Then, the weight and maybe other details about the particular specimen 18 can be entered in the system 1 (e.g. via the user interface 14) to compute the required volume or weight of fixative solution F based on predefined data or the like. It is also possible that dedicated and predefined or pre-calculated data are stored in a storage unit of the control unit C or system 1 for a plurality of particular specimens. In this case, the user merely enters some required data (type of biological organic (i.e. organ) sample; age and other data of the patient; dimensions of sample; and so on) based on which data the system 1 then computes the required volume or weight of the fixative solution using the stored data and without weighing the sample 18 (in the system 1). However, the weighing of the sample 18 can also be combined with the usage of stored data to increase the accuracy of the system 1.

The flexible bag 15 is preferably placed in the system 1 such that its opening 15a extends over the sealing means 22, particularly the sealing bar 23 provided in the treatment chamber 6. In case the delivery means 19 is in its delivery position, the opening 15a of the bag 15 can further be directly imposed on the delivery nozzle 19 when placing the bag 15 into the system 1, preferably onto the weighing device 16.

Then, the cover 5 is closed to sealably cover the treatment chamber 6. When doing so, the sealing bars 23, 23 are brought into a position being adjacent to each other enclosing the end of the flexible bag 15 preferably close to its opening 15a. An opening or slit S is provided between said sealing bars 23, 23 allowing the delivery means 19 to extend between said sealing bars 23, 23 and into the bag 15 when being in a delivery position.

Next, the system calculates or computes the required volume or weight, i.e. amount of fixative solution (e.g. formalin) to be delivered in the flexible bag 15 containing the biological organic sample 18 as a function of the sample 18 or the bag 15 with the sample 18, e.g. based on the weight of the sample 18 and/or other data stored in and/or (manually) entered into the system 1. The dosage of the fixative F can be linearly or non-linearly dependent on the weight or other data of the biospecimen 18. Preferably, the user can input further particular data regarding the biospecimen 18 as well as the period of storage and the like via the user interface 14 and prior to the computing of the ratio, based on which data the computed dosage of fixative F can be even more improved. The computing can be initiated either manually (e.g., via the user interface) or automatically.

It is noted that the cover 5 can also be closed after the computing of the amount of fixative F to be delivered into the flexible bag 15 has been terminated.

In step 2 (fixating step) as shown in FIG. 4, in case the delivery means is in its retracted position (see FIG. 3), the delivery means 19 is brought from its retracted position into its delivery position either manually or automatically. Therefore, the delivery means 19 is preferably automatically rotated about the longitudinal axis L of its upstream end 19a such that its bended downstream end 19b is moved into the flexible bag 15 thus extending into the flexible bag 15 to allow a delivery of the fixative solution into the flexible bag 15. It is noted that the delivery means 19 can be in the delivery position before placing the bag 15 on the weighing device in step 1 and must thus not be rotated before transferral of fixative F. In this case, the bag will be imposed on the delivery means 19 accordingly, i.e. as shown in FIG. 4 and described above (see step 1), such that a delivery of fixative F is enabled in step 2. In case the delivery means is manually rotated into its delivery position, the cover 5 can also be sealably closed after said manipulation.

After computing the required volume or weight of the fixative solution F, the system automatically transfers the computed volume or weight of fixative solution from the storage container 7 into the bag 15 by accordingly controlling the pump 10 and valve 11. The transfer command can be either given upon manual command input of the user via the user interface 14 or, in a preferred embodiment, automatically. The amount of the fixative solution F can automatically be checked gravimetrically or volumetrically by the same weighing device 16 as already used in step 1. To stop the transferral of fixative solution into the flexible bag 15, the system preferably automatically stops the pump 10 and closes the valve 11. However, it is also possible that the user can manually stop the transferral via the user interface 14, e.g. upon a visual or acoustic signal generated by the control unit C in case the pre-calculated or predefined ratio has been reached.

After the transfer operation is completed, the bag 15 can be evacuated and/or sealed either upon manual command input or preferably automatically as shown in step 3 (evacuating and sealing step) depicted in FIGS. (4 and) 5. As can be seen in FIG. 4, the treatment chamber 6 and thus also the flexible bag 15 are evacuated by means of the evacuation means 20. The withdrawal by suction is indicated by the arrow being directed in the suction direction, i.e. out of the treatment chamber 6 (or flexible bag 15). After or preferably before the minimum vacuum level has been reached, more preferred before starting the evacuation of the bag 15, the delivery means 19 is retracted from the flexible bag 15 into its sealing or retracted position as shown in FIG. 5. During evacuation, i.e. suction of air out of the treatment chamber 6, any escaping (toxic) fumes or vapours are drew off as well and preferably filtered off the air by a filtering means provided in the evacuation means 20.

It is noted that there might be provided a nozzle connected to the vacuum connection 21, i.e. being part of the evacuation means 20, which can be designed and moved the same way as the delivery means 19 and can be moved such that it extends into the flexible bag 15 for evacuating the bag, and after being evacuated, the nozzle can be retracted from the bag to allow a sealing of the bag 15 as described next.

When the evacuation has been completed, i.e. preferably when reaching the minimum vacuum level and when the delivery means 19 (and also a nozzle of the evacuation means 20) is in its sealing or retracted position, the sealing means 22 can be operated as described above to seal the flexible bag 15 containing the biological organic sample 18 as well as the defined amount of fixative solution F. The sealing command can be given automatically by the system 1 (control unit C) itself or upon manual command input via the user interface 14.

The flexible bags 15 with the sample 18 and the fixative F is then removed from the system 1 by opening the cover 5 (and thus releasing the flexible bag 15 from the sealing bars 23, 23). The sample 18 in the evacuated and sealed flexible bag 15 can then be transported to histology lab. Therefore, the sample in the bag 15 can be kept at room temperature or preferably below room temperature, e.g. at 4° C.

The method thus describes a user's defined fixation method which allows the same fixative/sample weight or volume ratio to be standardized and documented for improved quality control. Further, in case the bags 15 are evacuated and sealed, no fumes or vapours can (inadvertently) escape from the bag 15. Moreover, the dosage of fixative can be dramatically reduced to a minimum amount needed for fixation thus avoiding an unnecessary waste of (toxic) fixative.

It is noted that all steps after placing the flexible bag 15 into the system 1 (i.e. onto the holder 17, preferably onto the weighing device 16) and before removing the flexible bag 15 from the system 1 can be carried out automatically, including the closing and opening of the cover, weighing the sample 18, computing the dosage of the fixative F, moving/rotating the delivery means 19 (and nozzle of the evacuation means 20) from a retracted position to a delivery position and the other way around, transferring the fixative F from the storage container 7 to the flexible bag 15, evacuating the flexible bag 15 and sealing the flexible bag 15.

At the arrival of the sample 18 in the histology lap, the user (e.g. the pathologist or the pathologist assistant) will slice open the bag 15 and carry out grossing.

Thereafter, the following can be done:

Firstly, the flexible bag 15 can simply be resealed again as it is. Secondly, a new flexible bag 15 is utilized using the system 1 and method according to the invention, i.e. placing the bag 15 with the remaining sample 18 on the holder 17, preferably the weighing device 16, computing the required volume or weight of fixative solution F as a function of the remaining sample 18 or the bag 15 with the remaining sample 18, and automatically transferring the computed volume or weight of fixative solution F into the bag 15 and preferably subsequently evacuating and resealing the bag 15 for transport and/or storage.

Figure 6:
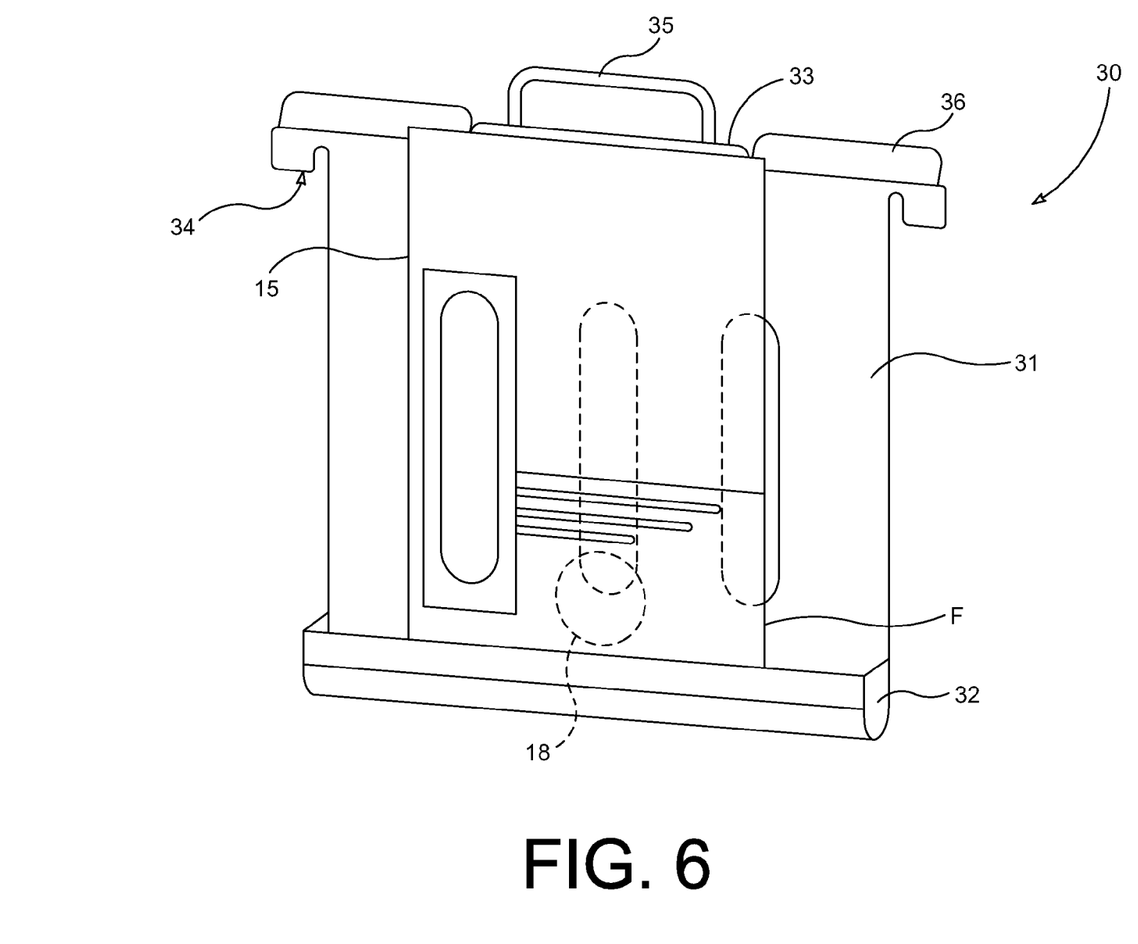
FIG. 6 shows a carrier according to the invention holding a flexible bag containing a biological organic sample in a fixative solution.

For storing the flexible bag 15 containing the at least one biological organic sample 18 in the fixative solution F, the invention is further directed to a carrier 30 as shown in FIG. 6. The carrier 30 comprises a frame 31 for holding the flexible bag 15. Further, the carrier 30 comprises a reservoir 32 which is arranged at the bottom of the frame 31 and preferably integrally formed with the frame 31. At least the reservoir 32 and maybe also the frame 31 are made of a material being resistant to the fixative solutions F. The reservoir 32 is dimensioned and, with respect to the frame 31, arranged such that any possible leakage of the flexible bag 15 can be collected inside the reservoir 32. Therefore, the reservoir 32 is arranged such that in case the flexible bag 15 is held by or attached to the frame 31 of the carrier 30, it is positioned right below or partially enclosing the flexible bag 15.

For holding the flexible bag 15, the carrier may further comprise a holding means 33 for easily attaching the flexible bag 15 to the frame 31 of the carrier 30 such that the flexible bag is arranged above and/or at least partially inside the reservoir 32. Said holding means 33 can be a clip or the like.

The carrier 30, particularly the frame 31 of the carrier 30 can further comprise a hanging means 34 for hanging the carrier 30 on and/or in a storage device like a storage cabinet 40, 50 being described in the following with respect to FIGS. 7 and 8. The hanging means 34 can, for instance, be designed as a hook or a clip or the like. However, the invention is not limited to any particular hanging means as long as the carrier 30 can be easily attached to a storage device.

The carrier can also comprise a handling means 35 like a knob or a handle as shown in FIG. 6 for easily handling the carrier 30 even in a case a heavy bag 15 is attached to the carrier 30.

Further, the carrier 30 can comprise an identification means (not shown) which can be removably attached to an exposed portion 36 of the frame 31 of the carrier 30. The identification means can be a tag, e.g. a handwritten label or a bar code label or a QR code label, or can be a chip, like an RFID-chip, or the like. The invention, however, is not limited to a particular identification means. It is also possible to alternatively or additionally attach an identification means onto the flexible bag 15 itself, e.g. in a pocket of the bag 15 as described above to include a requisition form or other documentation or information.

Figure 7:
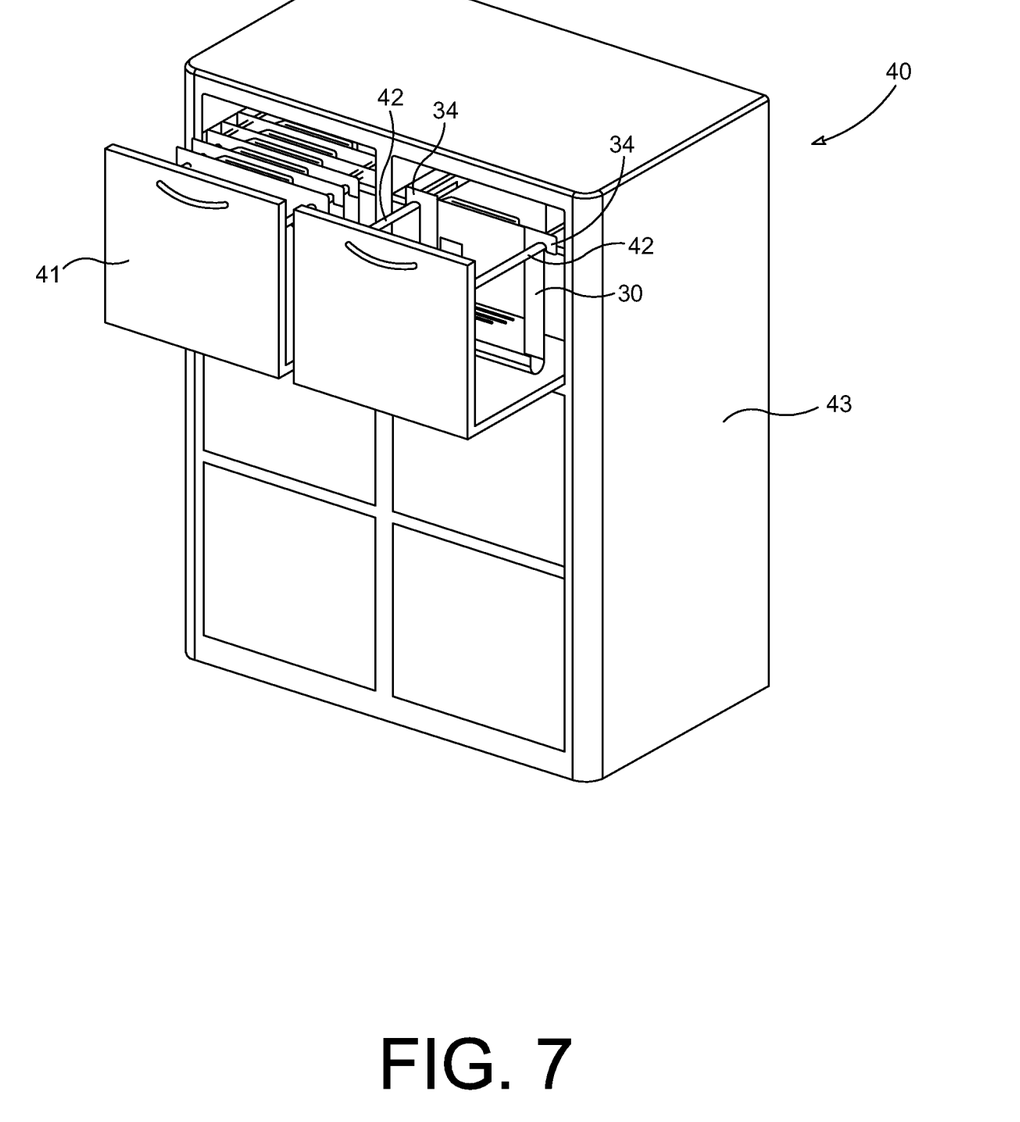
FIG. 7 shows a first embodiment of a storage cabinet according to the invention.
Figure 8:
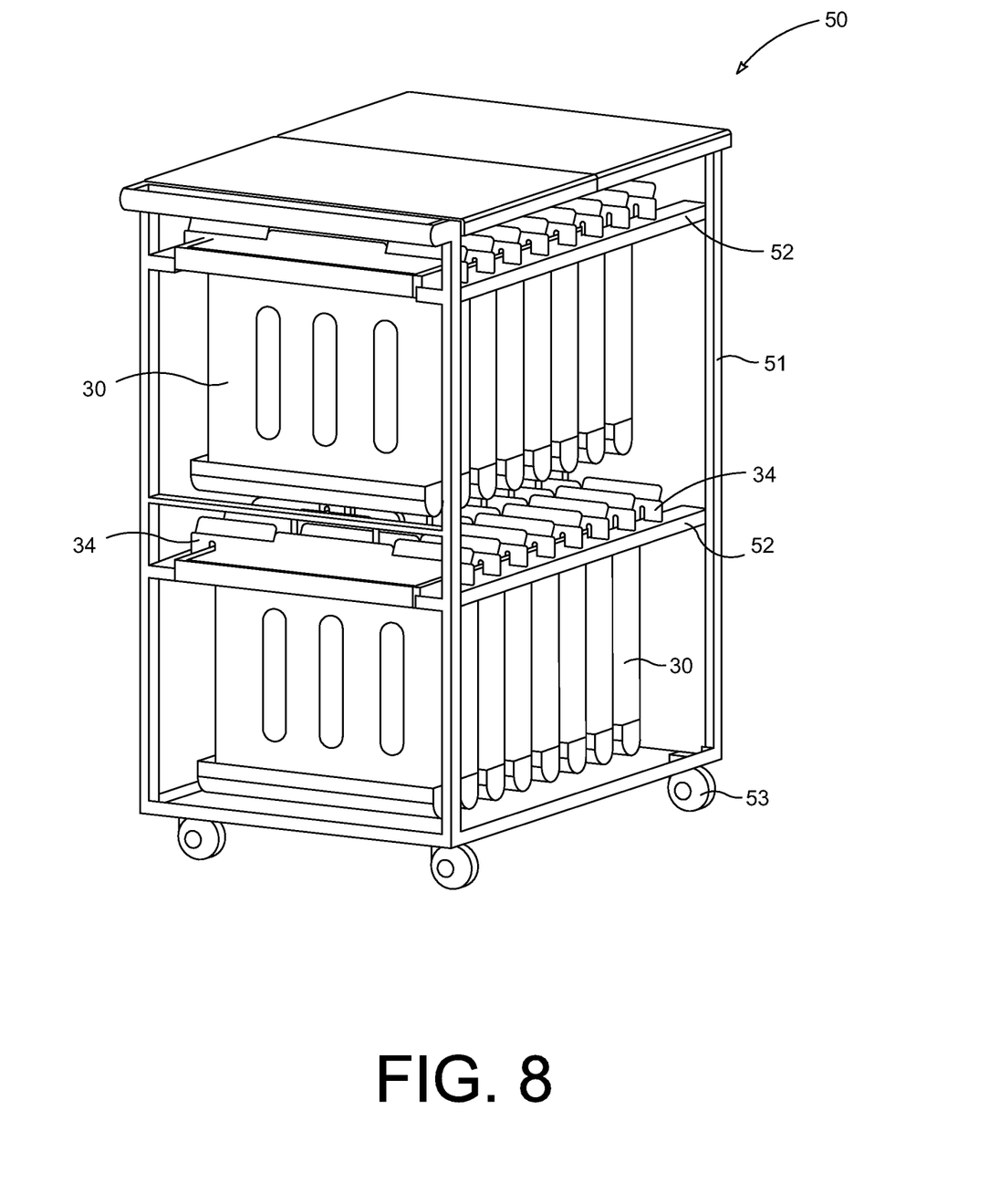
FIG. 8 shows a second embodiment of a storage cabinet forming a transfer trolley according to the invention.

FIGS. 7 and 8 show two embodiments of a storage cabinet for storing the carrier 30 according to the invention.

The storage cabinet 40 shown in FIG. 7 comprises a closed housing 43 and at least one or a plurality of doors 41 in which at least one or a plurality of the carriers 30 according to the invention can be stored. The storage cabinet 40 comprises receiving means 42 for receiving the hanging means 34 of the carrier 30 for storing the carrier 30 in a hanging file-type.

The storage cabinet 40 may further comprise a ventilation or exhaust system (not shown) for ventilating the storage cabinets 40 thus avoid toxic vapours escaping from the storage cabinet 40 in the unlikely case that a flexible bag 15 leaks. The storage cabinet 40 can also be provided with a warning device to warn the user in case toxic vapours are detected inside the storage cabinet. In a preferred embodiment, the reservoirs 32 of the carriers 30 are provided with detection means which may send an alarm signal to a control unit (not shown) of the storage cabinet also indicating the particular carrier 30 having the leaking flexible bag 15. The user can thus be informed about the leakage and preferably also about the particular bag 15 leaking by means of a visual and/or acoustic alarm.

The storage cabinet 40 can, preferably, also comprise wheels thus forming a transfer trolley to be movable like the storage cabinet 50 as shown in FIG. 8.

The storage cabinet 50 in FIG. 8 comprises a frame body 51, parts of which forming the receiving means 52 for receiving the hanging means 34 of the carrier 30 for storing the carrier 30 in a hanging file-type. The storage cabinet 50 comprises wheels 53 thus forming a transfer trolley to be movable.

It is again noted that the receiving means 42, 52 and the hanging means 34 are not limited to a particular geometry and design as long as an easy storage of the carrier 30 in or on the storage cabinet 40, 50 can be attained.

Figure 9:
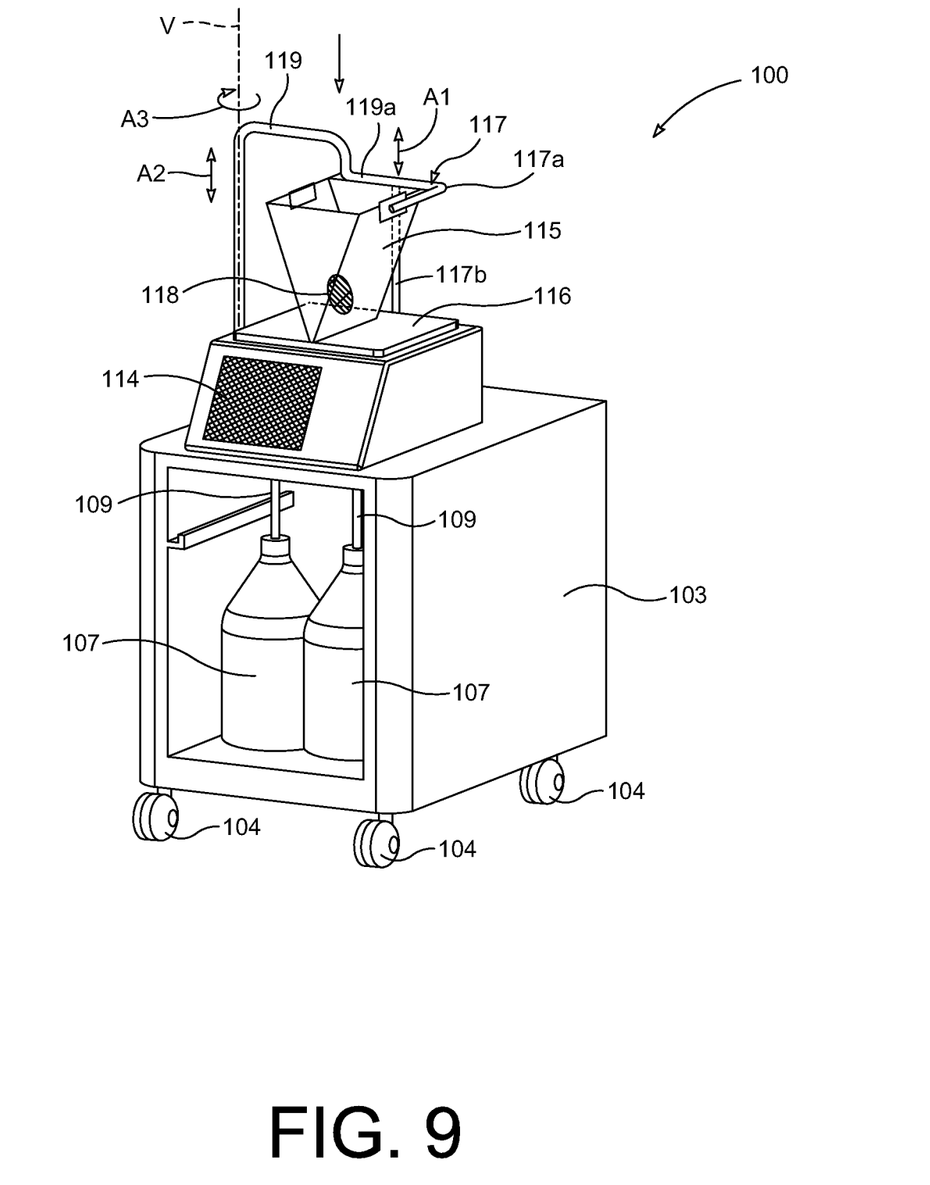
FIG. 9 shows a system for automatically dosing a fixative solution in a flexible bag containing a biological organic sample according to a second embodiment of the invention.

Turning to FIG. 9 showing another embodiment of a (dosing) system 100 according to the invention. The features being similar to the features of the first embodiment have been provided with the same reference numeral plus 100. It is hereby fully referred to the description of the first embodiment, as the correlated features have the same function and advantages as described above.

The system 100 also comprises a housing 103 in which at least one storage container 107 can be replacably stored. The system 100 can be provided with wheels 104 thus being movable. The storage containers 107 are connected via a storage line 109, respectively, to a delivery means 119 which opening 119a is directed downward towards and distant from a weighing device 116. The delivery line 109 is also provided with a pump and a valve (both not shown) as similarly shown in FIG. 2. At least the pump, the valve and the weighing device 116 are also controllable by a control unit (not shown) having a controller and a CPU. The system 100 also has a user interface 114, e.g. a touch screen or the like. Further, system 100 comprises a holder 117 for holding the flexible bag 115 containing the sample 118 upright on the weighing device 116.

In the embodiment shown in FIG. 9, the holder 117 comprises a U-shaped holding arm 117a which is preferably arranged above the weighing device 116 and surrounds the outlet of the delivery means 119 when seen in a top view (indicated by the arrow in FIG. 9). The U-shaped holding arm 117a is attached to the housing 103 by means of a shaft member 117b.

The flexible bag 115 can be attached to the U-shaped holding arm 117a in an upright position and being held open to allow a fixative solution F being delivered from the storage containers 107 via the storage line 109 and the delivery means 119 into the flexible bag 115. Therefore, the bag 115 can either be clipped to the exposing arms of the U-shaped holding arm 117a or the bag 115 can be put over these extending arm portions by imposing means either separately attached to the flexible bag 115 or integrally formed therewith. However, the invention is not limited to the design and arrangement of the holder 117 as long as it enables the bag 115 being placed in the system 100, preferably on the weighing device 116, in such a manner that the opening 115a of the bag 115 is kept open and below the opening 119a of the delivery means 119 for enabling a (automatically) computing of a required volume or weight of fixative solution F as a function of the sample or the bag 115 with the sample 118, and for enabling an automatic transfer of the computed volume or weight of fixative solution F from the storage container 107 into the bag 115.

The shaft 117b can be moveable in a vertical direction (as indicated by the double-pointed arrow A1 above the shaft 117b) such that the biospecimen 118 can always be securely placed on the weighing device 116 independent from the size of the bag 115. Further, also the extending arms of the U-shaped holding arm 117a can be designed to be moveable in a horizontal direction relatively toward or away from each other to be adaptable to any particular bag 115 size.

Moreover, the delivery means 119 can be selectively moveably between a delivery position thus extending into the bag 115, and a retracted position thus being retracted from the flexible bag 115. Therefore, the delivery means 119 can be rotatable about a vertical axis V and/or moveable along the vertical axis V as indicated by the arrows A2 and A3.

A method for automatically dosing a fixative solution F in the flexible bag 115 containing at least one biological organic sample 118 by using the system 100 as shown in FIG. 9 will be described in the following and is mainly similar to the method according to the first embodiment apart from the cover 5 as well as the evacuation means 20 and sealing means 22.

The method comprises the following steps: Firstly, the bag 115 with the sample 118 is placed in the system, preferably on the weighing device 116. Therefore, the flexible bag 115 is attached to or imposed on the holder 117 as described above such that the bag 115 is kept open with its opening 115a placed below the opening 119a of the delivery means 119. Secondly, the required volume or weight of a fixative solution F as a function of the sample 118 or the bag 115 with the sample 118 is computed individually as already described above with respect to the first embodiment. Thirdly, the computed volume or weight of fixative solution is automatically transferred from the storage container 107 into the bag 115. Therefore, the control unit controls the pump and valve accordingly to transfer the pre-calculated amount of fixative F from the storage container 107 via the delivery line 109 and the delivery means 119 into the flexible bag 115 as already described with respect to the first embodiment.

When the transferral of fixative has been finished, the flexible bag 115 can be evacuated and/or sealed separately in a subsequent step. However, it is also possible that an evacuation means is provided to the system 100 (see also the description regarding the first embodiment for further details) having a nozzle or the like being movable between a first position in which it extends into the flexible bag 115 and a second position in which it is retracted from the flexible bag 115. Further, the system, e.g. the extending arms of the U-shaped holding arm 117a, can be provided with a sealing means (e.g. sealing bars like the sealing bars 23, 23 of the first embodiment), respectively, which can seal the (evacuated) flexible bag 115 being filled with the required volume or weight of the fixative solution F.

Therefore, both the delivery means 119 and the nozzle of the evacuation means must be retracted from the flexible bag 115.

The invention is not limited to the above-described embodiments as long as being covered by the subject-matter of the following claims. It is noted that the features of a particular embodiment can be combined with or replaced by other (corresponding) features of any other embodiment.

The invention claimed is:

1. A system for automatically dosing a fixative solution in a flexible bag containing at least one biological organic sample, the system comprising:
   a holder to hold a flexible bag containing the biological organic sample upright in the system;
   a pump to transfer an amount of fixative solution from a storage container into the flexible bag;
   a control unit for controlling the pump to automatically transfer an amount of fixative solution from the storage container into the flexible bag; and
   a fixative solution delivery nozzle for discharging the amount of fixative solution from the storage container into the flexible bag, wherein the fixative solution delivery nozzle is moveable between a delivery position, in which the fixative solution delivery nozzle extends into the flexible bag, and a sealing or retracted position, in which the fixative solution delivery nozzle is retracted from the flexible bag.

2. The system of claim 1, further comprising a weighing device, wherein the holder is designed to hold the flexible bag containing the biological organic sample upright on the weighing device.

3. The system of claim 2, wherein the weighing device comprises a device for volumetrically and/or gravimetrically weighing.

4. The system of claim 2, wherein the weighing device comprises a load cell, and wherein the holder is attached to the weighing device in a fixed or removable manner.

5. The system of claim 1, further comprising evacuation means for evacuating the flexible bag, the evacuation means being controlled by the control unit.

6. The system of claim 1, further comprising sealing means for sealing the flexible bag, the sealing means being controlled by the control unit.

\* \* \* \* \*